(12) United States Patent
Witzmann et al.

(10) Patent No.: US 9,744,016 B2
(45) Date of Patent: *Aug. 29, 2017

(54) INCONTINENCE TREATMENT DEVICE (71) Applicant: Coloplast A/S, Humlebaek (DK)

(72) Inventors: Michael M. Witzmann, Shoreview, MN (US); Douglas A. Devens, Jr., Saint Paul, MN (US)

(73) Assignee: Coloplast A/S, Humlebaek (DK)

( * ) Notice: Subject to any disclaimer, the term of this patent is extended or adjusted under 35 U.S.C. 154(b) by 779 days.

This patent is subject to a terminal disclaimer.

(21) Appl. No.: 14/133,656

(22) Filed: Dec. 19, 2013

(65) Prior Publication Data

US 2014/0107403 A1    Apr. 17, 2014

Related U.S. Application Data (60) Continuation of application No. 13/589,189, filed on Aug. 20, 2012, now Pat. No. 8,636,644, which is a division of application No. 13/034,710, filed on Feb. 25, 2011, now Pat. No. 8,273,010, which is a continuation of application No. 12/815,440, filed on Jun. 15, 2010, now Pat. No. 8,550,979.

(30) Foreign Application Priority Data

Jun. 14, 2010   (DK) .................................. 2010 70262

(51) Int. Cl.
*A61F 2/00* (2006.01)
*A61B 17/04* (2006.01)
*A61B 17/00* (2006.01)

(52) U.S. Cl.
CPC ........ *A61F 2/0045* (2013.01); *A61B 17/0401* (2013.01); *A61B 2017/00805* (2013.01); *A61B 2017/0464* (2013.01); *A61F 2210/008* (2013.01); *A61F 2210/009* (2013.01); *A61F 2250/0007* (2013.01)

(58) Field of Classification Search
CPC ..................................................... A61F 2/0045
See application file for complete search history.

(56) References Cited

U.S. PATENT DOCUMENTS

2002/0188170 A1* 12/2002 Santamore ....... A61B 17/00234
                                                              600/37
2004/0002729 A1*  1/2004 Zamore ................. A61L 31/048
                                                              606/194

(Continued)

*Primary Examiner* — Catherine B Kuhlman
(74) *Attorney, Agent, or Firm* — Coloplast Corp., Coloplast A/S; Nick Baumann (57) ABSTRACT An incontinence treatment system includes a urethral support extending between a first end and a second end, a first connector attached to the first end of the urethral support and a second connector attached to the second end of the urethral support, and an energy source. At least one of the first connector and the second connector is a cross-linked polymer connector having a glass transition temperature between 40-70 degrees Celsius. In this regard, the cross-linked polymer connector is stretched to provide a stretched cross-linked polymer connector having a product length. The energy source is adapted to provide energy from an extracorporeal location through intact skin to shorten the stretched cross-linked polymer connector to an implant length that is less than the product length.

22 Claims, 11 Drawing Sheets

(56) References Cited

U.S. PATENT DOCUMENTS

| | | | | |
|---|---|---|---|---|
| 2005/0070829 A1* | 3/2005 | Therin | ............... | A61F 2/0045 602/1 |
| 2009/0137862 A1* | 5/2009 | Evans | ............... | A61B 17/0401 600/37 |
| 2009/0259092 A1* | 10/2009 | Ogdahl | ............... | A61F 2/0045 600/30 |
| 2011/0297161 A1* | 12/2011 | Deitch | ............... | A61B 17/0401 128/834 |

* cited by examiner

INCONTINENCE TREATMENT DEVICE

BACKGROUND

Devices for treating urinary incontinence include slings, supports, and other scaffold-like devices that are implanted in a patient's body to support the urethra.

One incontinence treatment device is a sub-urethral sling that is surgically implanted under the urethra. The implanted sling supports the urethra, which inhibits urine from leaking out of the urethra particularly during a provocative event (e.g., coughing or sneezing).

Implanting an incontinence treatment device and anatomically securing the device can be difficult and time-consuming. In addition, imperfect anatomical fixation or adjustment in the tension of the device relative to the urethra has the potential to produce suboptimal results in the treatment of urinary incontinence.

Other urinary incontinence treatment devices, such as injected bulking liquids, provide beneficial effects, but the beneficial effects of bulking liquids can potentially decrease over time, for example as the liquid is absorbed into the body.

Improved incontinence treatment devices and methods of implantation of the devices would be welcomed by both the patient and the surgical staff.

SUMMARY

One aspect provides an incontinence treatment device including a urethral support and first and second connectors. The urethral support extends between a first end and a second end and has porosity that is configured to allow tissue in-growth through the urethral support. The first connector is attached to the first end of the urethral support and the second connector is attached to the second end of the urethral support. At least one of the first connector and the second connector is a cross-linked polymer connector having a glass transition temperature between 40-70 degrees Celsius. The cross-linked polymer connector has an initial length that is elongated to an implant length that is greater than the initial length. Means for heating the cross-linked polymer connector from an extracorporeal location through intact skin is provided, thereby shortening the cross-linked polymer connector.

One aspect provides a device adapted to treat incontinence in a patient. The device includes a support having a first end and a second end; a first connector attached to the first end of the support and a second connector attached to the second end of the support; a first anchor coupled to the first connector and a second anchor coupled to the second connector; and a ferromagnet. At least one of the connectors is a cross-linked polymer connector. The device is implantable such that the anchors are fixed within a pelvis of the patient and tissue is grown through the support. The ferromagnet is attached around each cross-linked polymer connector between a midpoint of the cross-linked polymer connector and its respective anchor. The device includes means for shortening, through intact skin from an extracorporeal location, a length of the cross-linked polymer connector between the midpoint of the cross-linked polymer connector and its respective anchor.

One aspect provides a method of treating incontinence in a patient that includes implanting a support by suspending the support from a pair of connectors attached to tissue thereby supporting a urethra of the patient with an implanted support and a pair of implanted connectors. The method additionally includes evaluating the patient for incontinence, and reducing the incontinence of the patient by shortening a length of one of the pair of implanted connectors through intact skin from a location extracorporeal of the patient.

One aspect provides a method of treating incontinence in a patient that includes implanting in a healthcare setting a device having a support supporting a urethra of the patient, a cross-linked polymer connector extending between the support and an anchor attached to pelvic tissue of the patient, and a ferromagnet attached around the cross-linked polymer connector between a midpoint of the cross-linked polymer connector and the anchor. The method additionally includes evaluating the patient for incontinence after discharging the patient from the healthcare setting, and reducing incontinence of the patient by applying energy through intact skin of the patient thereby heating and shortening the cross-linked polymer connector between the midpoint of the cross-linked polymer connector and the anchor.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 5A is a perspective view, FIG. 5B is an axial cross-sectional view.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this application, skin is defined to be an organ including an epidermis upper layer, a hypodermis lower layer, and a dermis layer between the epidermis and hypodermis layers. Intact skin means skin in which the dermis layer is not compromised, which includes, as two illustrative examples, a dermis layer that has been incise but has healed post-surgically and a naturally occurring dermis layer that has not been incised in a surgical procedure.

In this application, "extracorporeal" means from outside of the body. The expression of acting on an implant from "an extracorporeal location through intact skin" means that the implant is adjusted from outside the patient without surgically accessing the implant or cutting into the skin.

People who are incontinent may be segregated into two groups: those with hyper-mobile urethras and those whose urethras are not hyper-mobile. A hyper-mobile urethra will translate into alignment with an exit of the bladder, thus creating a "straight-shot" pathway from the bladder that allows urine to escape from the bladder and out of the urethra. Physicians have developed an evaluation to determine if the patient has a hyper-mobile urethra. The evaluation entails the placement of an indicator stick into the longitudinal axis of the urethra such that a portion of the indicator stick extends distally out of the patient's body (those of skill in the art refer to the evaluation as the "Q-tip™ test"). The patient is prompted to initiate a provocative event, for example a cough or a tightening of the abdominal muscles, and the physician observes the indicator stick for movement (this evaluation is sometimes referred to as the "cough test"). Movement of the indicator stick indicates that the longitudinal axis of the urethra is moving, which is indicative of the patient having a hyper-mobile urethra.

The urethra is normally supported by connective and other tissues. Over time, and particularly with parous women, the support of the urethra erodes, giving rise to hyper-mobility of the urethra. As described above, hyper-mobile urethras are susceptible to the undesirable leaking of urine during provocative events such as sneezing, laughing, or coughing (which is sometimes referred to as stress urinary incontinence).

The implant described herein supports the urethra to treat incontinence. In addition, the implant described herein is adjustable post-implant without surgically accessing the implant (e.g., from outside of the patient's body) to modify/increase the support provided to the urethra from the implant over time.

Figure 1A:
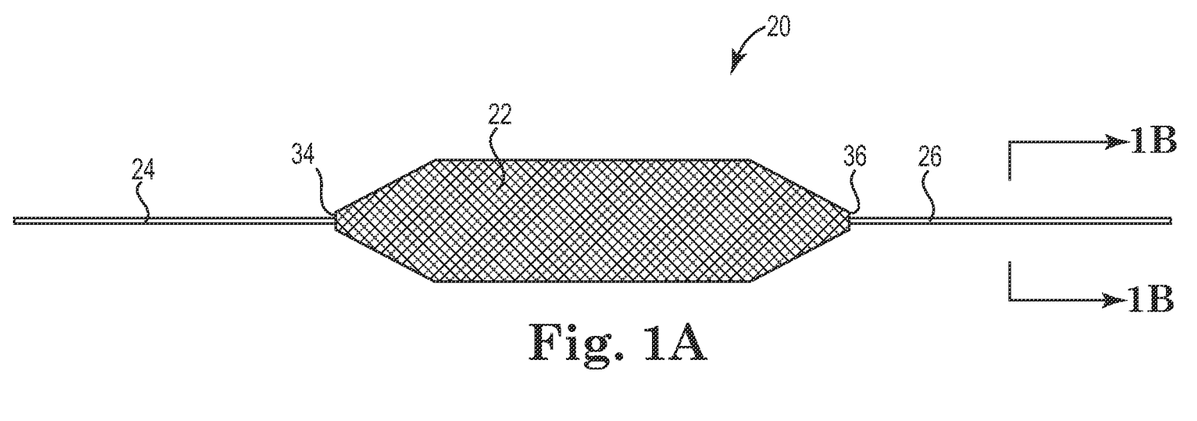
FIG. 1A is a top view of one embodiment of an incontinence treatment device including a support and connectors extending from the support.

FIG. 1A is a top view of one embodiment of an incontinence treatment device 20 including a urethral support 22 and a pair of connectors 24, 26. In one embodiment, the urethral support 22 extends between a first end 34 and a second end 36, and the first connector 24 is connected to the first end 34 and a second connector 26 is connected to the second end 36 of the urethral support 22.

The urethral support 22 is selected to be tissue compatible for implantation into a human body and is configured to allow tissue ingrowth through its structure to anchor the support 22 in the body after implantation and healing. Suitable material for the support 22 includes autograft material (the patient's own tissue), allograft material (tissue from a cadaver), xenograft material (tissue from another species), or synthetic materials such as woven fabrics, meshes, nonwoven fabrics, meshes, fibrillated fibers, or spun and fibrillated fibers that are provided with voids (pores) configured to allow tissue ingrowth into the support. The pores are generally larger, on average, than 75 μm.

The support 22 is suitably shaped as a rectangular sling, a multi-arm support having an X-shape with four arms extending from a body, a T-shaped sling having two transverse arms and one longitudinal body, or other pelvic support shapes.

In one embodiment, the support 22 is a knitted monofilament polypropylene mesh having a mass per area between approximately 15-35 g/m$^2$ with a pore size between approximately 500-1500 μm and a thickness of approximately 260 μm. This mesh is thin and light weight (i.e., the basis weight is less than approximately 35 g/m$^2$) to provide a thin and comfortable mesh that is less likely to erode tissue that contacts the mesh and less likely to be sensed through the tissue layers by the patient. Other suitable materials for the support 22 include fabrics formed from polyester, polyethylene, silicone, urethanes, polyurethanes, copolymers, or block copolymers of these or suitably similar polymeric materials. Suitable such knitted monofilament polypropylene mesh is available from Coloplast Corp., Minneapolis, Minn. Other suitable woven polypropylene mesh material is available from, for example, HerniaMesh, Chivasso, Italy.

The connectors 24, 26 are provided as strands that are employed to suspend the urethral support 22 in a patient's body to support the urethra (female) or to elevate and compress the urethra (male). In one embodiment, at least one of the connectors 24, 26 is provided as a cross-linked polymer connector having a glass transition temperature between 40-70° C. The cross-linked polymer connector, for example connector 26, is provided as an amorphous polymer that is initially irradiated to cause internal cross-linking of the polymer molecules. The cross-linking sets the molecules in a preferred orientation. The cross-linked polymer connector 26 is stretched from an initial length to a stretched, final product length. When the stretched cross-linked polymer connector is heated, or energy is otherwise provided to overcome the stretched orientation of the molecules, the molecules relax and return to the cross-linked, preferred orientation associated with the initial length of the cross-linked connector 26. In this manner, the cross-linked polymer connector 26 is heat-shrinkable between its stretched, final product length and its initial length.

Figure 1B:
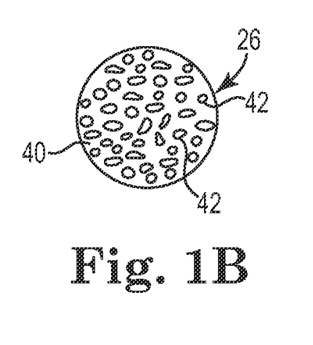
FIG. 1B is a cross-sectional view of one of the connectors of the device illustrated in FIG. 1A.

FIG. 1B is a cross-sectional view of the cross-linked polymer connector 26. In one embodiment, the cross-linked polymer connector 26 includes an amorphous polymer 40 that is cross-linked and metal particles 42 that are doped or otherwise dispersed into the polymer 40. The metal particles 42 can be heated, and when heated, cause the polymer 40 to be heated above its glass transition temperature to allow the oriented molecules relax to their initial cross-linked state. In one embodiment, the metal particles 42 are ferromagnetic and respond to induction heating, for example as provided by an inductive heat source producing an alternating current field.

Suitable amorphous polymers 40 that are configured for cross-linking include nylon 12, high density polyethylene, and polyester, as three examples. In one example, an amorphous nylon 12 polymer is selected having a glass transition temperature between 40-70° C. The nylon 12 is irradiated with an electron beam source to cross-link the molecules of the nylon 12. The nylon 12 is stretched and the cross-linked molecules are stretched and oriented. At temperatures below 40° C., the nylon 12 is stable to local temperatures (the temperature of a healthy human body is approximately 37° C.). For temperatures above 40° C., approaching 70° C., the nylon 12 has sufficient molecular mobility to allow the oriented molecules to move or relax from the stretched and oriented state back to the initial cross-linked orientation, thus shrinking in length when heated.

In one embodiment, the metal particles 42 are provided in the polymer 40. The metal particles 42 are configured to be heated and conduct the heat to the polymer 40 to transition the polymer 40 between the stretched/oriented state back to the initial cross-linked (short) state. Suitable materials for the metal particles 42 include metal elements and alloys of metal, for example iron, or an iron alloy including NiCu, or an iron alloy including CoPd.

Figure 1C:
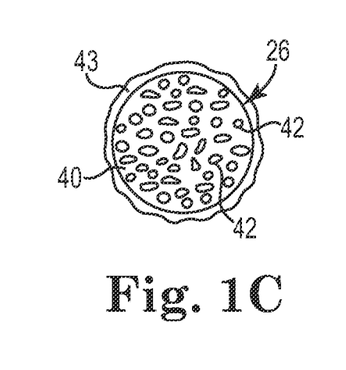
FIG. 1C is a cross-sectional view of the connector of FIG. 1A including an insulating sheath.

The metal particles 42 are provided to conduct heat to the polymer 40. FIG. 1C illustrates an embodiment where the cross-linked polymer connector 26 is co-axially extruded, for example, or otherwise coated to include a co-axial sheath 43 of a low thermal conductivity material provided to insulate the cross-linked polymer connector 26, when heated, from adjacent tissue. Suitable materials having low thermal conductivity include foams (for example polyolefin foam) or polymer sheaths that are not doped with metal particles. Thus, in one embodiment the illustrated cross-linked polymer connector 26 is provided with an insulating exterior cover/sheath 43 of a material having a thermal conductivity that is lower than the thermal conductivity of the polymer 40/particle 42 system.

Figure 2A:
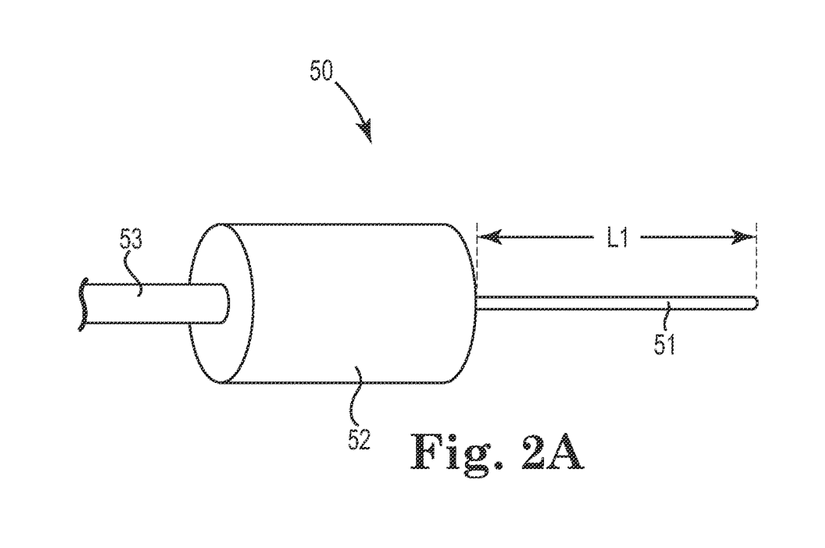
FIG. 2A is a perspective view of one embodiment of a process for extruding a strand suitable for use as one of the connectors illustrated in FIG. 1B.

FIG. 2A is a perspective view of one embodiment of a process 50 for forming a strand 51 suitable for use as one of the cross-linked polymer connectors 26. In one embodiment, the strand 51 is formed by an extruder 53 that delivers amorphous polymer through a fiber-forming spinnerette 52.

Figure 2B:
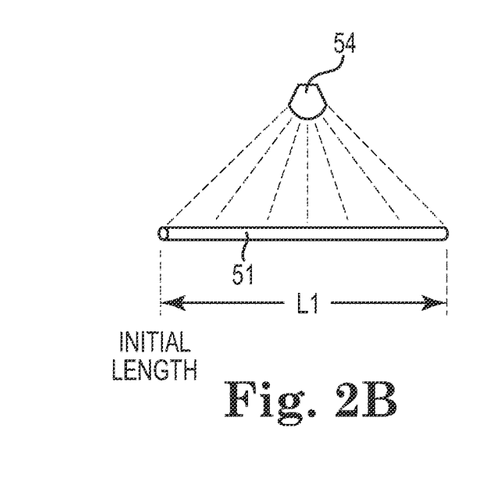
FIG. 2B is a side view of one embodiment of a length of the strand illustrated in FIG. 2A being irradiated to cross-link molecules of the strand.

FIG. 2B is a side view of one embodiment of the strand 51 being irradiated by an irradiation source 54 to cross-link molecules of the strand 51. The radiation causes the strand 51 to retain a memory of its initial length L1.

Figure 2C:
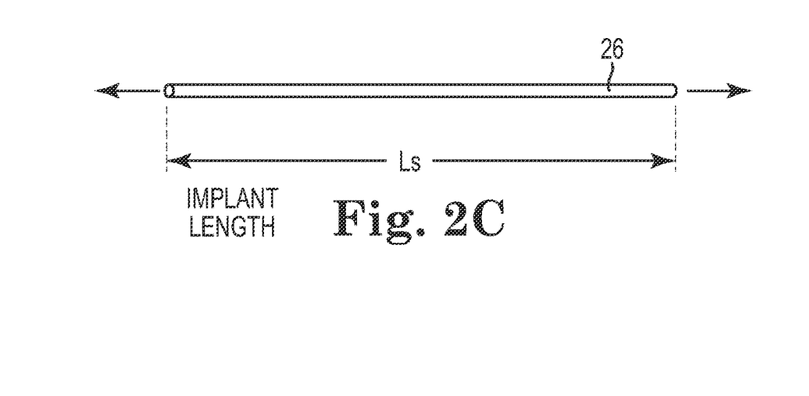
FIG. 2C is a side view of the cross-linked strand illustrated in FIG. 2B stretched to orient the molecules in the cross-linked strand and provide the strand at an appropriate implant length.

FIG. 2C is a side view of the strand 51 stretched to a stretched implant length Ls to form the cross-linked connector 26. The energy or the force that is employed to stretch the cross-linked connector 26 from its initial length L1 to the stretched length Ls (e.g., the implant length Ls) overcomes the energy of the cross-linked molecular orientation to orient (or re-orient) the molecules in the connector 26 at the desired implant length Ls.

Figure 2D:
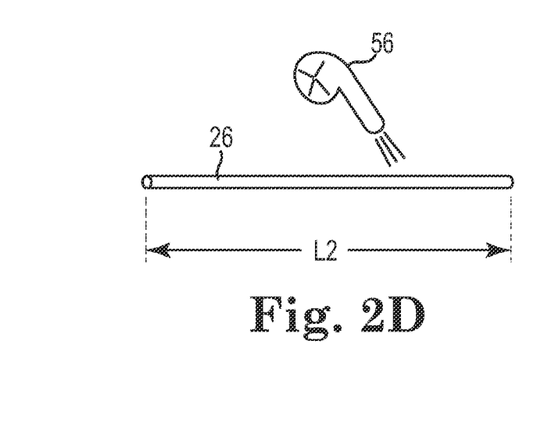
FIG. 2D is a side view of the stretched strand illustrated in FIG. 2C heated to relax the oriented molecules in the cross-linked strand and shrink the strand from the implant length to a shorter length.

FIG. 2D is a side view of the stretched strand/connector 26 heated to relax the oriented molecules in the cross-linked strand/connector 26. When the connector 26 is heated, from a heat source or energy source 56 such as an inductive energy source, the molecules relax and the connector 26 shrinks to a shortened length L2 (shorter than the implant length Ls). Additional applied energy or continuous heating will shrink the connector 26 back to the cross-linked orientation associated with the un-stretched, initial length L1 (FIG. 2B). Suitable energy sources 56 are those that are able to penetrate the human body through intact skin and include microwave energy sources or inductively coupled devices that provide an alternating current filed that couples with the metal particles 42 (FIG. 1B) to heat the metal particles 42, thus heating and shrinking polymer 40.

As mentioned above, in one embodiment the connector 26 is fabricated from an amorphous polymer 40 that is doped with metal particles 42. The above discussion applies to connectors or strands formed from a cross-linkable amorphous polymer, such as nylon 12 that does not include metal particles. An un-doped cross-linked polymer system, when irradiated, stretched, and suitably heated (e.g., via radiation or convection), will behave as described above. In one embodiment, the metal particles 42 are incorporated into the amorphous polymer 40 to allow the connector 26 to receive extracorporeal heat sources such as microwaves, inductors, and other wireless energy transmitters and become heated.

Figure 3A:
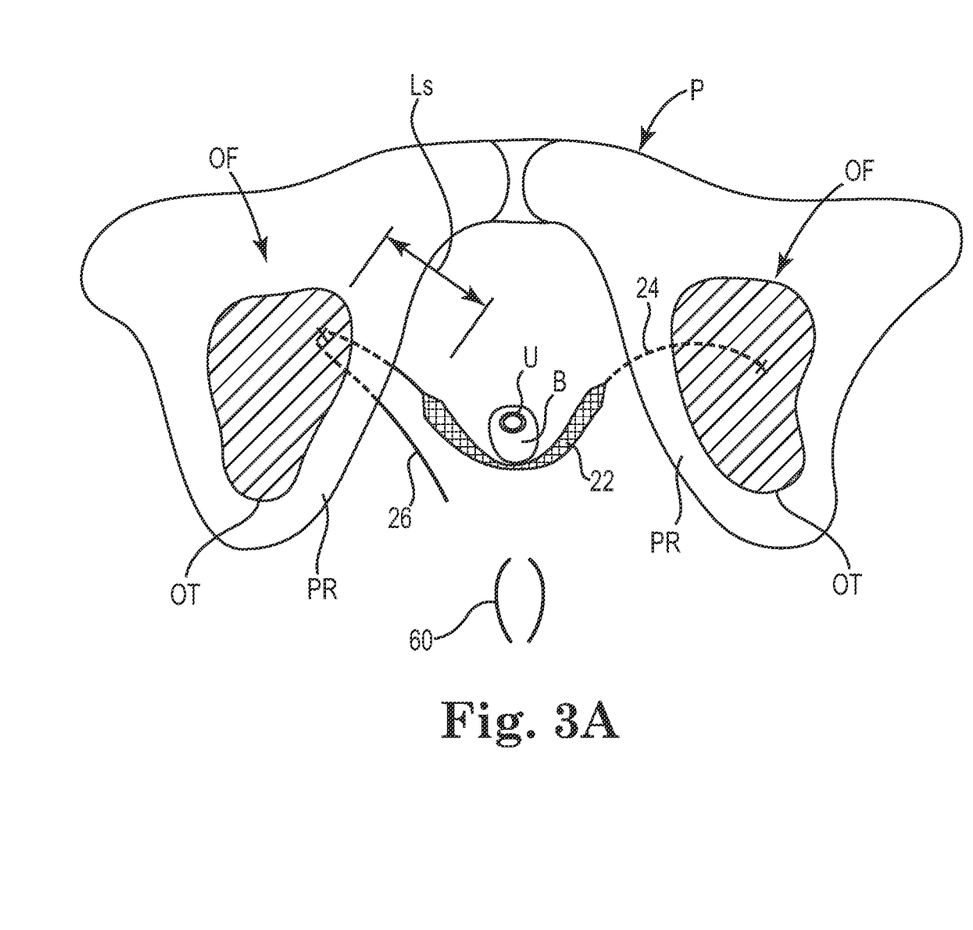
FIG. 3A is a schematic view of the incontinence treatment device illustrated in FIG. 1A implanted in a patient.

FIG. 3A is a schematic view of the incontinence treatment device 20 attached to tissue to support a urethra U of the patient. In one embodiment, the device 20 is attached between opposing obturator membrane tissue OT of opposing obturator foramen OF, although the device is acceptably attachable to other pelvic tissue. The urethral support 22 is generally placed against bulbous spongiosum tissue B of the urethra to decrease possible erosion of the urethra itself. The connectors 24, 26 extend from the support 22 around a portion of the pubic ramus PR bones and are terminated in the obturator membrane tissue OT. In one embodiment, the patient is a female and the incontinence treatment device 20 supports the urethra U without compressing the urethra U. In one embodiment, the patient is a male and the incontinence treatment device 20 supports the urethra U by elevating and compressing at least a portion of a bulb the urethra U.

In one embodiment, the incontinence treatment device 20 is introduced through a single perineal incision 60 along an inside out pass that places the connectors 24, 26 around a portion of the pubic ramus PR. For example, the surgeon places the connectors 24, 26 either digitally with a finger or with a tool into the incision 60 and guides the each connector 24, 26 inwardly for termination with pelvic tissue, for example a ligament or the membrane tissue OT of the obturator foramen OF.

The incontinence treatment device 20 is implanted in the patient such that the support 22 is suspended under the urethra U in contact with the bulbous spongiosum tissue B, and the connectors 24, 26 are terminated into tissue. When implanted, the connector 26 extends between the support 22 and the membrane tissue OT and has the stretched implant length Ls. The device 20 is initially adjusted during the implantation surgery to ensure that an appropriate level of support is provided to the urethra U to reduce or eliminate the incontinent condition of the patient. Thereafter, the surgeon closes the minimally invasive incision 60 according to acceptable practices. The incontinence treatment device 20 provides the patient with a level of continence immediately after implantation due to the suspension provided by the support 22 to the urethra, or due to the elevation and compression (in males) that is provided to the urethra U.

Figure 3B:
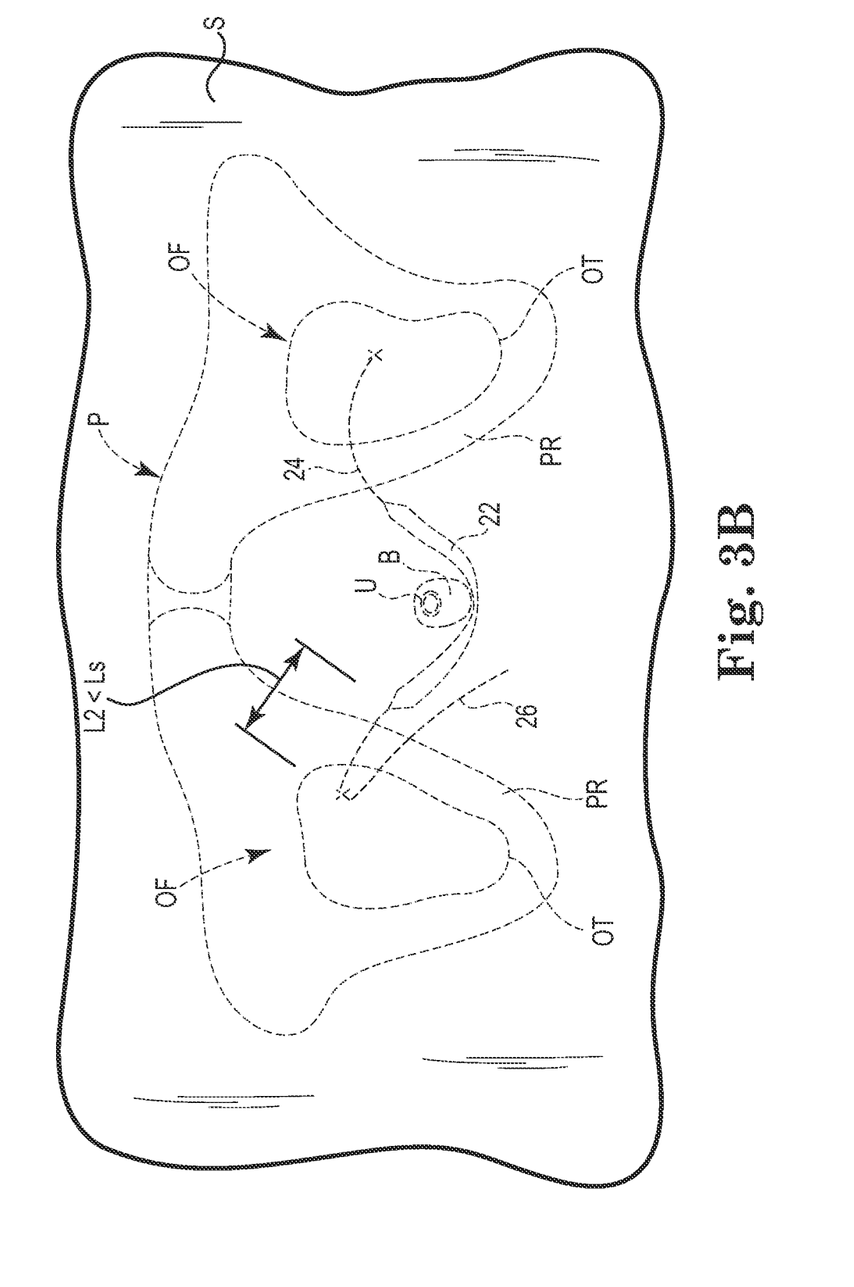
FIG. 3B is a schematic view of the implanted incontinence treatment device adjusted from an extracorporeal location through intact skin of the patient.

FIG. 3B is a schematic view of the implanted incontinence treatment device 20. The patient, through the healing process or other activities, might eventually experience a reduced level of continence characterized by leaking of urine from the urethra. The prior solution, in such cases, would be to schedule the patient for surgery, incise tissue of the patient, and adjust the tension of the support or the connectors manually inside of the body. In contrast, the implanted incontinence treatment device 20 provides the patient and the surgeon with the ability to adjust the connector 26 from an extracorporeal location through intact skin S by shortening the cross-linked polymer connector 26 from the implanted length Ls (FIG. 3A) to a shorter length L2. The shortened connector 26 "tightens" and applies increased beneficial support to urethra U to reduce or eliminate the patient's incontinence.

In one embodiment, the surgeon adjusts the connector 26 in a clinical setting by applying an extracorporeal energy source, for example an inductive heating device providing alternating current energy through the patient's skin S, without forming an incision, and the energy is directed to the connector 26. The metal particles 42 (FIG. 1B) are inductively heated and cause local heating of the polymer 40. Heating of the polymer 40 relaxes the orientation of the molecules of the connector 26 and allows the molecules to return toward the initial orientation associated with the cross-linked state having initial length L1 (FIG. 2B). In this manner, the connector 26 heat shrinks from the final stretched implant length Ls (FIG. 3A) to a shorter length L2 (FIG. 2D). The shorter length L2 is less than the stretched implant length Ls, such that the connector 26 shrinks in response to local heating to provide additional urethral support and improved continence. If the energy source is applied for a sufficiently long duration of time, the connector 26 will heat shrink from the final product length, or stretched implant length Ls, all the way back to the initial length L1.

Figure 4:
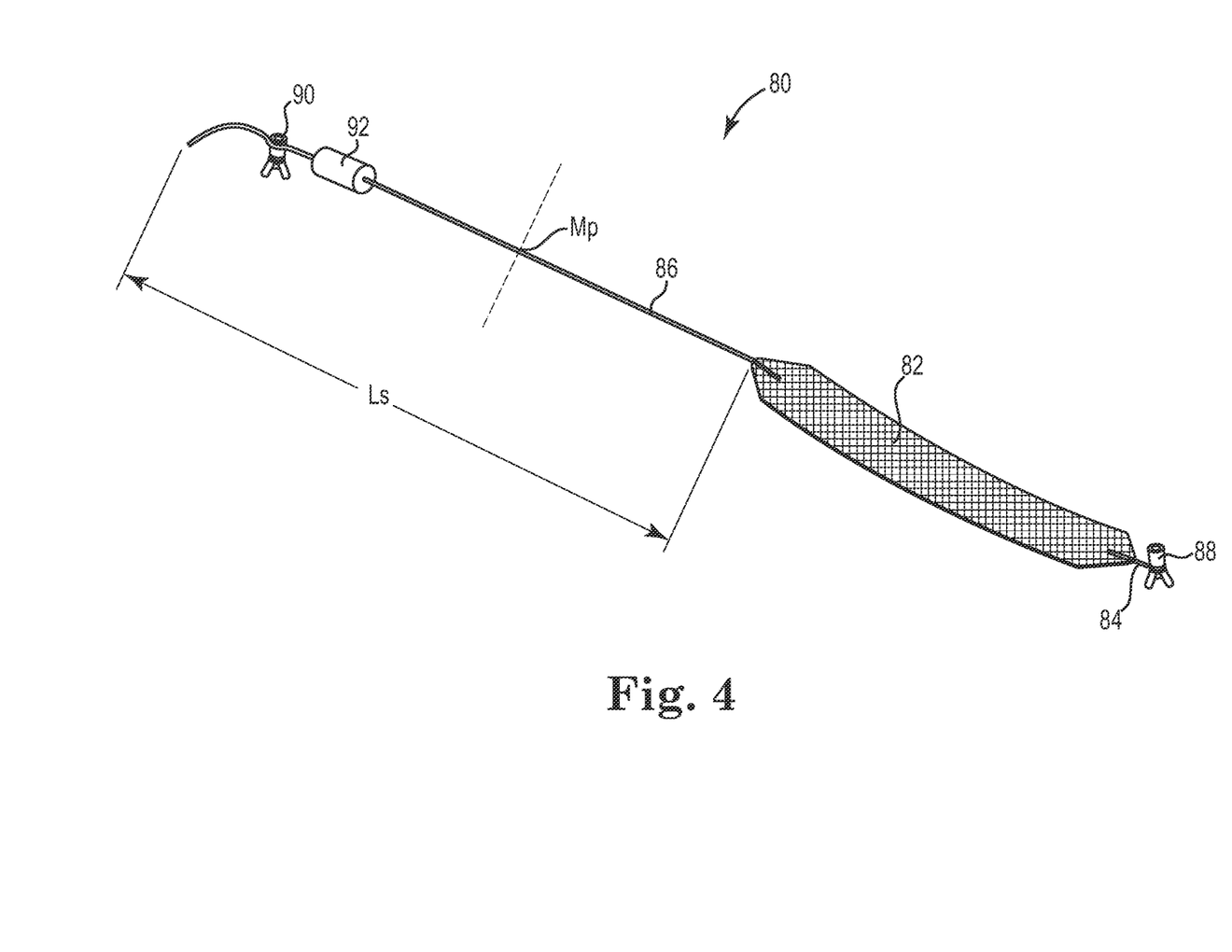
FIG. 4 is a perspective view of one embodiment of an incontinence treatment device including a ferromagnet placed around a heat-shrinkable connector.

FIG. 4 is a perspective view of one embodiment of an incontinence treatment device 80. The device 80 includes a support 82, connectors 84, 86 extending from the support 82, anchors 88, 90 attached to the connectors 84, 86, respectively, and a ferromagnetic unit 92 attached to the connector 86.

The support 82 is similar to and suitably fabricated from the materials described above for support 22.

In one embodiment, at least one of the connectors 84, 86 is fabricated to provide a cross-linked polymer connector having a glass transition temperature between 40-70° C. In one embodiment, the first connector 84 is provided as a standard polypropylene suture material and the second connector 86 is provided as a heat shrinkable cross-linked polymer connector as described above for connector 26.

In one embodiment, the anchors 88, 90 are adjustable anchors that move relative to the connectors 84, 86, respectively. In one embodiment, at least one of the anchors 88, 90 is fixed relative to its respective connector 84, 86.

The ferromagnetic unit 92 is provided to receive energy and be heated, and conduct the heat to the connector 86, which allows the connector 86 to heat shrink as the molecules in a cross-linked polymer connector 86 relax in response to the heat energy. For example, in one embodiment energy is delivered to the patient's body from an extracorporeal location from an induction heating device. The ferromagnetic unit 92 couples with the field from the induction heating device and becomes heated. The heated ferromagnetic unit 92 conducts heat to the connector 86, allowing the connector 86 to be heated to a temperature above its glass transition temperature, which relaxes the molecules in the connector 86 to permit heat shrinking of the connector 86.

The heat delivered to the connector 86 is proportional to the length of the ferromagnetic unit 92. It has been discovered that the amount of shrinkage delivered to the connector 86 is a function of the length of the ferromagnetic unit 92. With this in mind, in one embodiment the ferromagnetic unit 92 is placed around less than half of the implant length Ls of the connector 86. In one embodiment, the ferromagnetic unit 92 is placed around the connector 86 closer to the second anchor 90 than to the support 82. That is to say, in one embodiment the ferromagnetic unit 92 is placed on the connector 86 between a midpoint Mp of the connector 86 and the anchor 90 to heat and shorten that portion of the connector 86. In one embodiment, the ferromagnetic unit 92 has a length between 0.5-6.0 cm, and preferably the ferromagnetic unit 92 has a length of approximately 2 cm.

In one embodiment, the ferromagnetic unit 92 is placed on the connector 86 between a midpoint Mp of the connector 86 and the anchor 90 to heat and shorten that portion of the connector 86 and not heat the length of the cross-linked polymer connector 86 between the midpoint Mp of the connector 86 and the support 82.

Figure 5A:
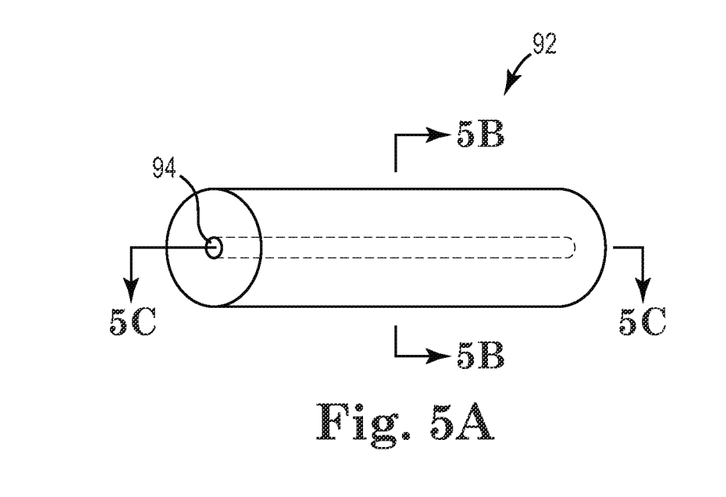
Figure 5B:
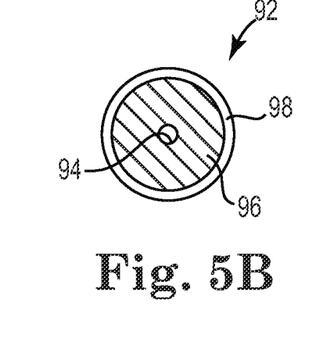
Figure 5C:
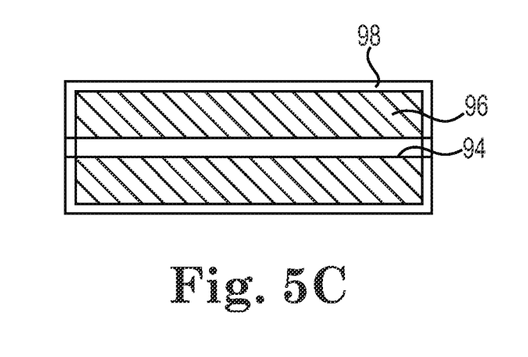
FIG. 5C is a longitudinal cross-sectional view of the ferromagnet illustrated in FIG. 4.

FIG. 5A is a perspective view, FIG. 5B is an axial cross-sectional view, and FIG. 5C is a longitudinal cross-sectional view of the ferromagnet unit 92. In one embodiment, the ferromagnetic unit 92 is provided as a cylinder having an axial hole 94 extending the length of the cylinder. The axial hole 94 is sized to receive and fit snuggly around the connector 86 in a heat-conducting configuration.

In one embodiment, the ferromagnetic unit 92 includes a core 96 of material and a thermal insulator 98. The core 96 of material is configured to respond to induction heating, and in one embodiment is provided as an alloy of NiCu or an alloy of CoPd. The ferromagnetic unit 92 is heatable to heat the connector 86, and is preferably tailored to minimize overheating and/or heating of the adjacent tissue. For example, in one embodiment the core 96 is selected to have a Curie temperature that is higher than the glass transition temperature of the connector 86. In this configuration, the ferromagnetic unit 92 would cease to heat once it becomes paramagnetic as it reaches its Curie temperature. In this manner, the ferromagnetic unit 92 is self-regulating and is designed to have a ceiling temperature above which it will not heat. For example, in one embodiment the connector 86 has a glass transition temperature of between 40-70° C. and the ferromagnetic unit 92 is fabricated to have a Curie temperature of between 60-75° C. As an example, in one embodiment the cross-linked polymer connector 86 is heat shrinkable at a temperature above 43 degrees Celsius, and the ferromagnetic unit 92 has a Curie temperature of approximately 60 degrees Celsius such that the ferromagnetic unit 92 will inductively heat to a temperature of 60 degrees Celsius or less to effectively heat the connector 86 without undesirably over heating the surrounding tissue.

The thermal insulator 98 is provided around the core 96 to ensure that the temperature of the ferromagnetic unit 92 does not become so hot as to deleteriously affect the patient. In one embodiment, the thermal insulator 98 is provided as a ceramic or a pyrolytic carbon sleeve disposed around an exterior surface of the core 96.

Figure 6A:
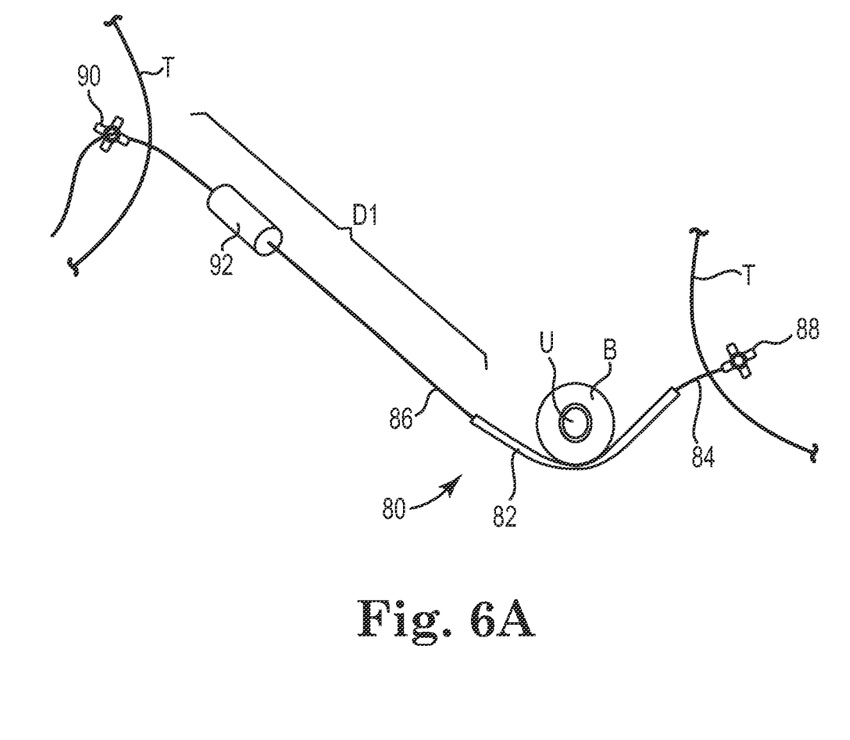
FIG. 6A is a schematic view of the incontinence treatment device illustrated in FIG. 4 implanted in a patient.

FIG. 6A is a schematic view of the incontinence treatment device 80 implanted in a patient. The anchors 88, 90 are fixed into tissue T and the connectors 84, 86 extend to the support 82 to suspend it under the urethra in contact with the bulbous spongiosum B tissue. The ferromagnetic unit 92 is closer to the second anchor 90 than it is to the support 82 such that a distance D1 is established between an end of the support 82 and the tissue T. In one embodiment, the incontinence treatment device 80 is implanted through a minimally invasive incision and suspended between the membranes of the opposing obturator foramen of the patient.

The device 80 is adjusted by the surgeon during surgery to ensure that an appropriate level of support is provided to the urethra U to reduce or eliminate the incontinent condition of the patient. Thereafter, the surgeon closes the minimally invasive incision according to acceptable practices. The incontinence treatment device 80 provides the patient with a level of continence immediately after implantation due to the suspension provided by the support 82 to the urethra, or due to the elevation and compression (in males) that is provided to the urethra U.

The implanted incontinence treatment device 80 provides the surgeon with the ability to adjust the connector 86 from an extracorporeal location through intact skin of the patient, thereby shortening the cross-linked polymer connector 86 and applying increased beneficial support to urethra U.

Figure 6B:
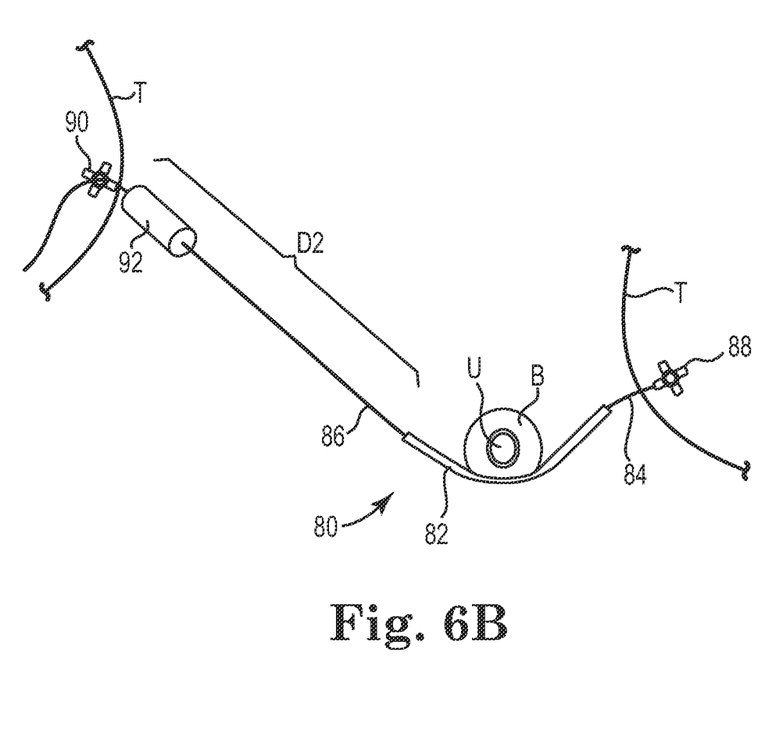
FIG. 6B is a schematic view of the incontinence treatment device illustrated in FIG. 6A adjusted from an extracorporeal location through intact skin of the patient.

FIG. 6B is a schematic view of the incontinence treatment device 80 as implanted and adjusted from an extracorporeal location through intact skin of the patient. There can be times when the patient discovers the presence of stress urinary incontinence, and the device 80 is configured to treat the stress urinary incontinence in a clinical setting. In one approach, the patient meets with the surgeon to discuss the incontinence, and the surgeon evaluates the level of incontinence, for example with the "cough test" described above. If the surgeon determines that stress urinary incontinence is present, the connector 86 is shortened from a location extracorporeal from the patient, without an incision, to reduce or eliminate the stress urinary incontinence.

In one embodiment, the surgeon applies an energy field through the intact skin of the patient, and the energy heats the ferromagnetic unit 92. The heated ferromagnetic unit 92 transfers heat to the connector 86, which warms a portion of the connector 86 above the glass transition temperature of the cross-linked polymer connector 86, thus allowing the molecules of the connector 86 to relax and shrink the connector 86 from the distance D1 (FIG. 6A) to distance D2.

Small changes in the length of the connector 86 will result in increased support to urethra U. In this regard, the length of the connector 86 need not be adjusted from the stretched implant length Ls all the way back to the much shorter initial length L1. The surgeon, as guided by experience, will briefly apply the energy to the connector 86, repeat the cough test, and iterate this process until a suitable level of continence for the patient is achieved.

In one embodiment, the ferromagnetic unit 92 has a length between 0.5-4 cm and is inductively heatable through intact skin to heat and thereby shorten only that portion of the connector 86 that is under the ferromagnetic unit 92 and that portion of the connector 86 that is within one length of the ferromagnetic unit 92.

Figure 7:
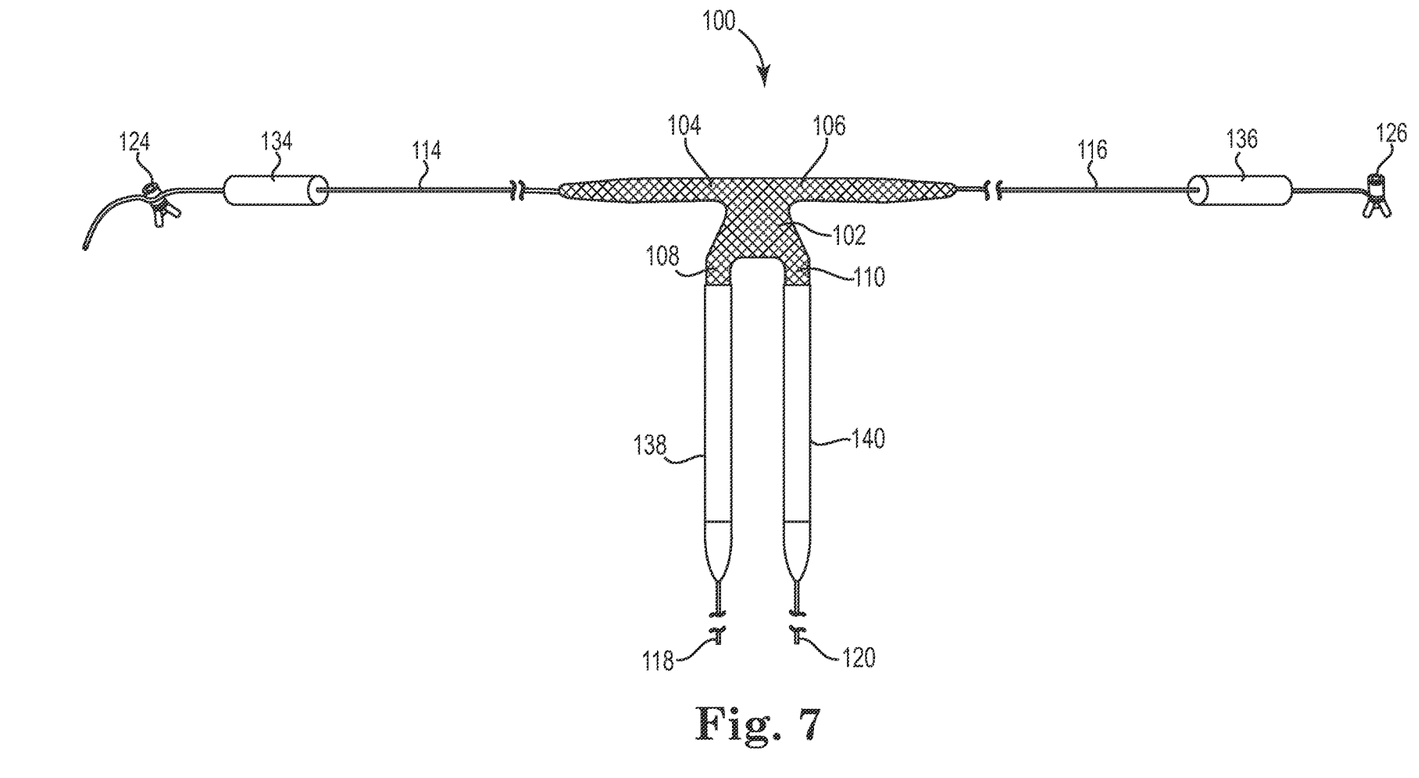
FIG. 7 is a top view of one embodiment of an incontinence treatment device including a pair of trans obturator arms, each provided with a connector and a ferromagnet, and a pair of suprapubic arms.

FIG. 7 is a top view of one embodiment of an incontinence treatment device 100. The device 100 includes a support body 102, a pair of trans obturator arms 104, 106 extending from the support body 102, a pair of suprapubic arms 108, 110 extending from the support body 102 and connectors 114, 116, 118, 120 each extending from a respective one of the arms. The support body 102 and the arms 104, 106, 108, 110 are each suitably fabricated from the materials described above for the support 22 (FIG. 1A).

In one embodiment, the connectors 114, 116 are provided with anchors 124, 126, respectively. The anchors 124, 126 include anchors that are fixed to the respective connectors, anchors that are movable relative to their connectors, or combinations of fixed and adjustable anchors.

One or more of the connectors 114, 116, 118, 120 is configured to be heat shrinkable consistent with the embodiment described above in FIG. 1A including the cross-linked polymer that is doped with metal particles or the embodiment described above in FIG. 4 including the cross-linked polymer provided with a ferromagnet. For example, in one embodiment the connectors 114, 116 are each provided as a cross-linked polymer connector have a glass transition temperature between 40-70° C. and include a ferromagnetic unit 134, 136, connected around a respective one of the connectors 114, 116. In another embodiment, all of the connectors 114, 116, 118, 120 are provided as heat shrinkable connectors (anchorless or with anchors as determined to be suitable for the surgical application).

In one embodiment, the incontinence treatment device 100 is surgically implanted into a patient via a single, minimally invasive incision in which the anchors 124, 126 are attached to a membrane extending over an opposing one of the obturator foramen to suspend the trans obturator arms 104, 106 across the pelvis, and the suprapubic arms 108, 110 are tunneled and terminated subcutaneously within the patient suprapubically. In one embodiment, the suprapubic arms 108, 110 are provided with optional removable sleeves 138, 140, respectively, that are employed to assist in the placement of the suprapubic arms 108, 110 suprapubically. The sleeves 138, 140 are removed from the arms 108, 110 after the arms are placed suprapubically within a patient.

Figure 8:
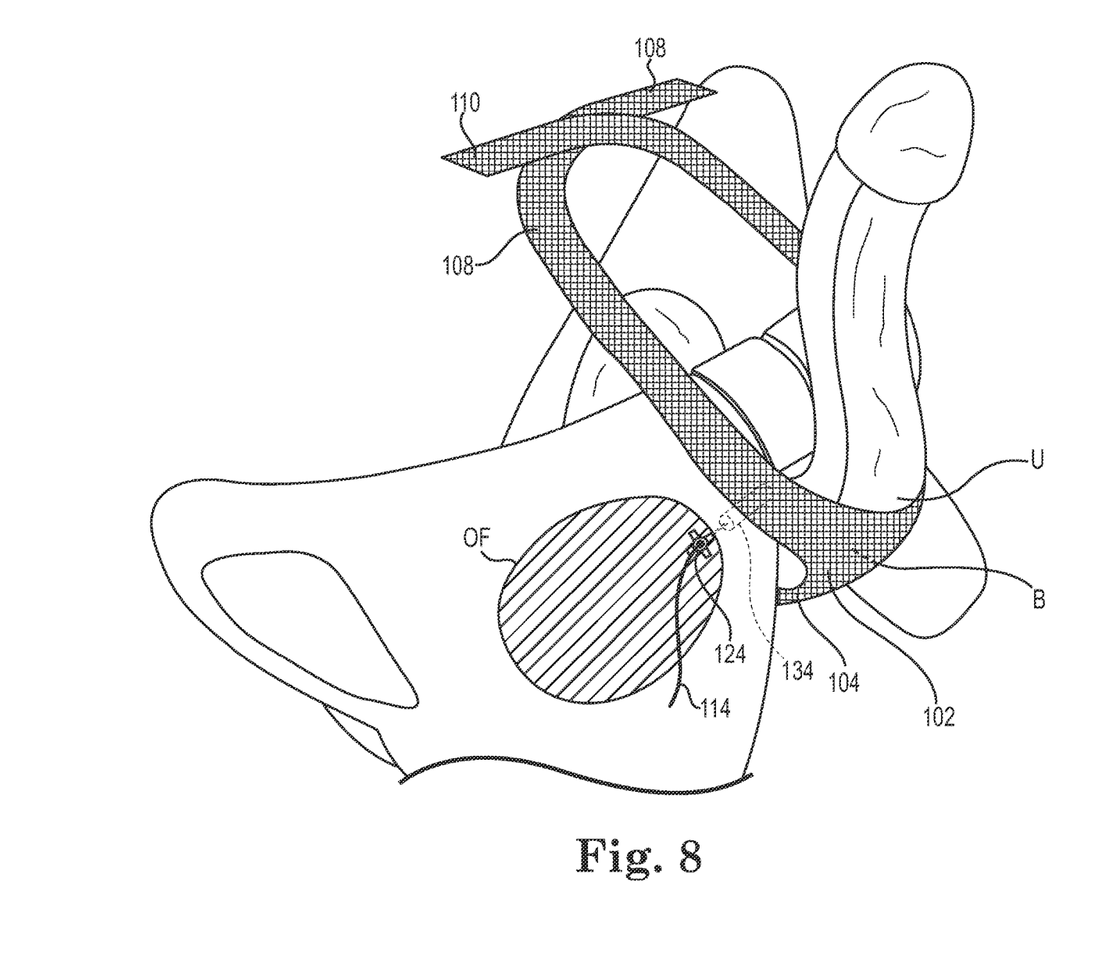
FIG. 8 is a schematic view of the incontinence treatment device illustrated in FIG. 7 implanted in a patient.

FIG. 8 is a schematic view of the incontinence treatment device 100 implanted in a male patient. The illustration presents a sub-dermal view of the location of the support body 102 relative to the ventral urethral bulb B of the patient. The trans obturator arms 104, 106 extend between membranes covering the obturator foramen OF. The suprapubic arms 108, 110 are tunneled and terminated subcutaneously within the patient suprapubically.

The tension in the connectors 114, 116 is adjustable surgically via the anchors 124, 126 that tension the support body 102 to elevate and compress the ventral urethral bulb B of the patient. The suprapubic arms 108, 110 are tunneled subcutaneously to compress the perineal urethra U. The surgeon adjusts the tension/elevation of the support body 102 via the anchors 124, 126, and adjusts the compression of the support body 102 against the ventral urethral bulb B of the patient by selectively tightening the suprapubic arms 108, 110. This surgical adjustment of the two pairs of arms may be done incrementally until the surgeon achieves the desired coaptation of the urethra U through the elevation and compression of the ventral urethral bulb B of the patient.

Thereafter, the tension in the connectors 114, 116 is adjustable post-operatively through the intact skin of the patient (without forming an incision) to address instances of recurring incontinence post-surgically consistent with the embodiments described above.

Figure 9:
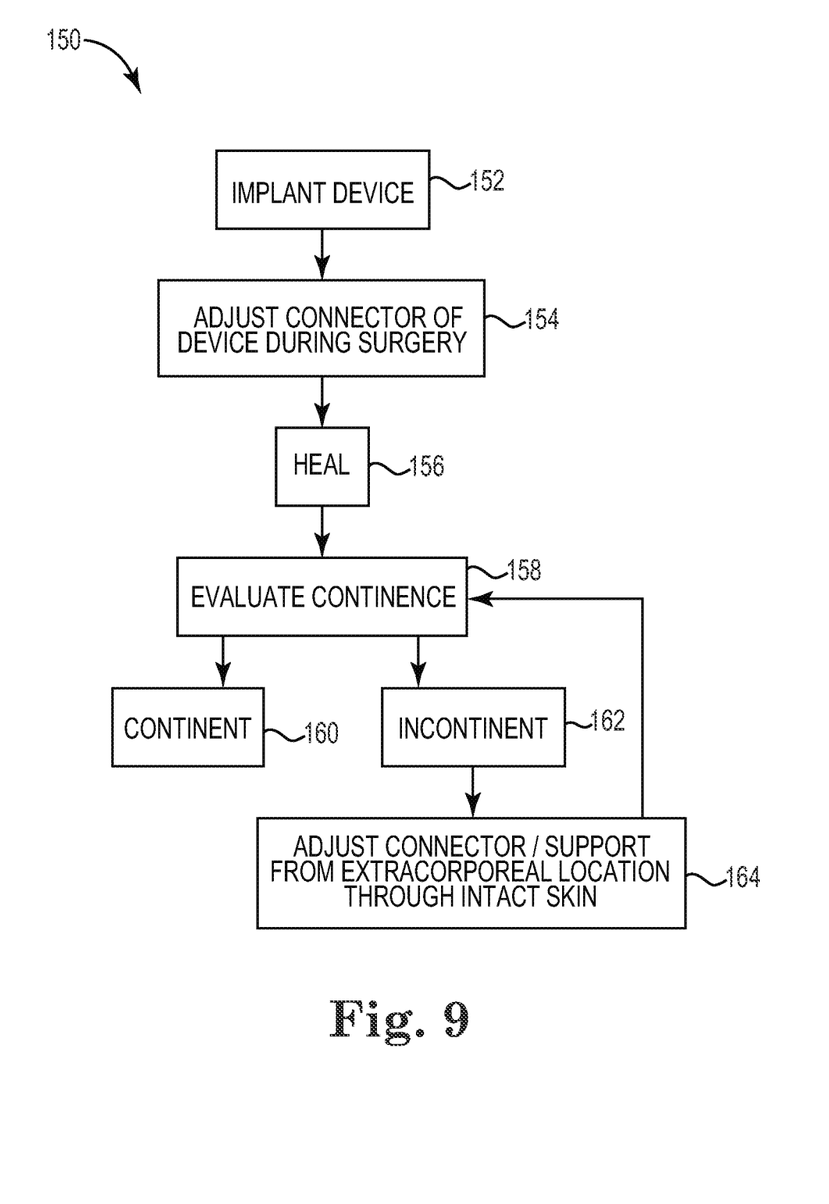
FIG. 9 is a flow diagram of one embodiment of a method of treating incontinence in a patient.

FIG. 9 is a flow diagram 150 of one embodiment of a method of treating incontinence in a patient. The method includes implanting the device at 152 and adjusting one or more connectors of the device during surgery at 154. Consistent with the surgical implantation of a medical device, the patient is discharged from a hospital or day care surgery center and allowed to heal at 156. The patient, for various reasons, may experience the recurrence of undesirable discharge of urine from the urethra (incontinence). The method provides means for addressing postsurgical incontinence by evaluation of the continence of the patient at 158 by a medical professional, for example through conducting a cough test or other suitable test. One example of the cough test includes an indicator, such as an absorbent stick, placed in the patient's urethra prior to the patient being prompted to cough or otherwise voluntarily stress the abdominal area. The indicator is observed for movement (which indicates hypermobility of the urethra) and 40 urine discharge from the urethra. If the medical professional determines that the patient does not have a hypermobile urethra or urine discharge, the patient is deemed to be continent at 160. Alternatively, urine discharged from the urethra indicates incontinence at 162. Embodiments described herein provide for the adjustment of a connector or of the support of the urinary incontinence device at 164 from an extracorporeal location as applied through intact skin in an office setting to adjust/elevate/compress or otherwise provide improved support to the urethra.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. An incontinence treatment system comprising:
   a urethral support extending between a first endmost end and a second endmost end;
   a first connector attached to the first endmost end of the urethral support and a second connector attached to the second endmost end of the urethral support, at least one of the first connector and the second connector is a cross-linked polymer connector having a glass transition temperature between 40-70 degrees Celsius, the cross-linked polymer connector stretched to provide a stretched cross-linked polymer connector having a product length; and
   an energy source;
   wherein the energy source is adapted to provide energy from an extracorporeal location through intact skin and shorten the stretched cross-linked polymer connector to an implant length that is less than the product length;
   wherein the cross-linked polymer connector comprises a core having metal particles dispersed in a polymer and an insulating sheath disposed around the core, the insulating sheath having a thermal conductivity that is lower than a thermal conductivity of the core of the cross-linked polymer connector.

2. The incontinence treatment system of claim 1, wherein the urethral support is porous and configured to allow tissue in-growth through the porous urethral support.

3. The incontinence treatment system of claim 1, wherein the urethral support is porous with an average pore size larger than 75 µm.

4. The incontinence treatment system of claim 1, wherein the urethral support comprises autograft material.

5. The incontinence treatment system of claim 1, wherein the urethral support comprises allograft material.

6. The incontinence treatment system of claim 1, wherein the urethral support comprises xenograft material.

7. The incontinence treatment system of claim 1, wherein the urethral support comprises a synthetic woven material.

8. The incontinence treatment system of claim 1, wherein the urethral support comprises a synthetic nonwoven material.

9. The incontinence treatment system of claim 1, wherein the urethral support comprises a mesh.

10. The incontinence treatment system of claim 1, wherein the urethral support comprises fibrillated fibers.

11. The incontinence treatment system of claim 1, wherein the urethral support is a knitted monofilament polypropylene mesh having a mass per area between approximately 15-35 g/m² with a pore size between approximately 500-1500 µm and a thickness of approximately 260 µm.

12. The incontinence treatment system of claim 1, wherein the urethral support is a rectangular sling.

13. The incontinence treatment system of claim 1, wherein the urethral support has a body and a multiplicity of arms extending from the body.

14. The incontinence treatment system of claim 1, wherein the metal particles are ferromagnetic particles.

15. The incontinence treatment system of claim 14, wherein the energy source is an inductive heat source.

16. The incontinence treatment system of claim 1, further comprising:
   a first anchor coupled to the first connector and a second anchor coupled to the second connector.

17. The incontinence treatment system of claim 16, wherein at least the first anchor is an adjustable anchor that is movably attached along the first connector.

18. The incontinence treatment system of claim 16, wherein the first anchor is an adjustable anchor that is movably attached along the first connector and the second anchor is an adjustable anchor that is movably attached along the second connector.

19. The incontinence treatment system of claim 16, wherein the first anchor is fixed in place relative to the first connector and the second anchor is an adjustable anchor that is movably attached along the second connector.

20. The incontinence treatment system of claim 1, further comprising:
   a ferromagnetic unit attached to the stretched cross-linked polymer connector.

21. The incontinence treatment system of claim 20, wherein the ferromagnetic unit is placed around less than half of the stretched cross-linked polymer connector.

22. The incontinence treatment system of claim 20, wherein the ferromagnetic unit includes an outer surface insulator disposed at an exterior surface of the ferromagnetic unit.

* * * * *